United States Patent
El Kouby-Benichou et al.

(10) Patent No.: US 11,363,971 B2
(45) Date of Patent: *Jun. 21, 2022

(54) SYSTEMS AND METHODS FOR ESTIMATING A THREE-DIMENSIONAL POSE

(71) Applicant: Colgate-Palmolive Company, New York, NY (US)

(72) Inventors: Vincent El Kouby-Benichou, Montreuil (FR); Olivier Giroud, Courbevoie (FR); Thomas Serval, Neuilly-sur-Seine (FR); Yann Nicolas, Neuilly-sur-Seine (FR)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/301,675

(22) Filed: Apr. 12, 2021

(65) Prior Publication Data
US 2021/0228112 A1 Jul. 29, 2021

Related U.S. Application Data

(63) Continuation of application No. 17/012,186, filed on Sep. 4, 2020, now Pat. No. 11,006,862, which is a (Continued)

(51) Int. Cl.
*G08B 23/00* (2006.01)
*A61B 5/11* (2006.01)
(Continued)

(52) U.S. Cl.
CPC ........ *A61B 5/1127* (2013.01); *A46B 15/0002* (2013.01); *A46B 15/0006* (2013.01);
(Continued)

(58) Field of Classification Search
CPC . A61B 5/1127; A61B 5/1128; A46B 15/0002; A46B 15/0006;
(Continued)

(56) References Cited

U.S. PATENT DOCUMENTS

| | | | |
|---|---|---|---|
| 6,786,732 B2 | 9/2004 | Savill et al. | |
| 8,330,823 B2 | 12/2012 | Gordon | |

(Continued)

FOREIGN PATENT DOCUMENTS

| | | |
|---|---|---|
| CN | 104660646 | 5/2015 |
| CN | 106998900 | 8/2017 |

(Continued)

OTHER PUBLICATIONS

Chang et al., 2008, "Playful toothbrush," CHI 2008 Proceedings—Kid's Stuff:363-372.

(Continued)

*Primary Examiner* — Tanmay K Shah

(57) ABSTRACT

A motion tracking element for an oral hygiene element such as a toothbrush. The motion tracking element may be detachably coupled to the oral hygiene element. The motion tracking element may include a body having an outer surface, a portion of the outer surface having a pattern that includes a plurality of indicators with a non-circular shape. The indicators may be flush with and form part of the outer surface. A plurality of visual markers may be located on the outer surface, each of the visual markers having a circular shape. The plurality of visual markers may be formed integrally with the body. A method for estimating a pose of an oral hygiene device may be achieved using the motion tracking element.

20 Claims, 5 Drawing Sheets

Related U.S. Application Data continuation of application No. 16/220,117, filed on Dec. 14, 2018, now Pat. No. 10,799,155.

(60) Provisional application No. 62/611,112, filed on Dec. 28, 2017.

(51) Int. Cl.
  *G06T 7/70* (2017.01)
  *A61C 17/00* (2006.01)
  *A46B 15/00* (2006.01)
  *G06T 7/246* (2017.01)
  *G06K 9/62* (2022.01)

(52) U.S. Cl.
  CPC ............ *A61B 5/1128* (2013.01); *A61C 17/00* (2013.01); *G06T 7/251* (2017.01); *G06T 7/70* (2017.01); *A46B 2200/1066* (2013.01); *G06K 9/6293* (2013.01); *G06T 2207/10016* (2013.01); *G06T 2207/30036* (2013.01); *G06T 2207/30196* (2013.01)

(58) Field of Classification Search
  CPC ... A46B 2200/1066; A61C 17/00; G06T 7/70; G06T 7/251; G06T 2207/30196; G06T 2207/30036; G06T 2207/10016; G06K 9/6293
  USPC ....................................................... 340/573.1
  See application file for complete search history.

(56) References Cited

U.S. PATENT DOCUMENTS

| | | | |
|---|---|---|---|
| 8,920,340 B2 | 12/2014 | Trivedi et al. | |
| 8,920,746 B2 | 12/2014 | Kennedy et al. | |
| 9,586,135 B1 | 3/2017 | Capper et al. | |
| 9,606,110 B2 | 3/2017 | Gittins et al. | |
| 9,700,395 B2 | 7/2017 | Hohlbein et al. | |
| 10,086,262 B1 | 10/2018 | Capper et al. | |
| 2009/0215015 A1 | 8/2009 | Chu | |
| 2016/0257009 A1 | 9/2016 | Godlieb et al. | |
| 2017/0069083 A1 | 3/2017 | Vetter et al. | |
| 2017/0238692 A1 | 8/2017 | Sarubbo et al. | |
| 2018/0078347 A1* | 3/2018 | Falkel | A61B 5/0088 |
| 2018/0132602 A1 | 5/2018 | Gatzemeyer | |
| 2018/0192765 A1* | 7/2018 | Jeanne | A46B 15/0006 |

FOREIGN PATENT DOCUMENTS

| | | |
|---|---|---|
| CN | 107028672 | 8/2017 |
| RU | 2526672 | 8/2014 |
| RU | 2534519 | 11/2014 |
| WO | 2013/155203 | 10/2013 |
| WO | 2016/020803 | 2/2016 |
| WO | 2017/157411 | 9/2017 |

OTHER PUBLICATIONS

Flagg et al., 2011, "An intelligent toothbrush: Machines for Smart Brushing," retrieved from the internet: URL:http://www.annaflagg. com/AnIntelligent Toothbrush(Flagg).pdf.

International Search Report and Written Opinion of International Searching Authority issued in PCT/US2018/065607 dated May 22, 2019.

Marcon et al., 2016, "Toothbrush motion analysis to help children learn proper tooth brushing," computer vision and image understanding 148:34-45.

* cited by examiner

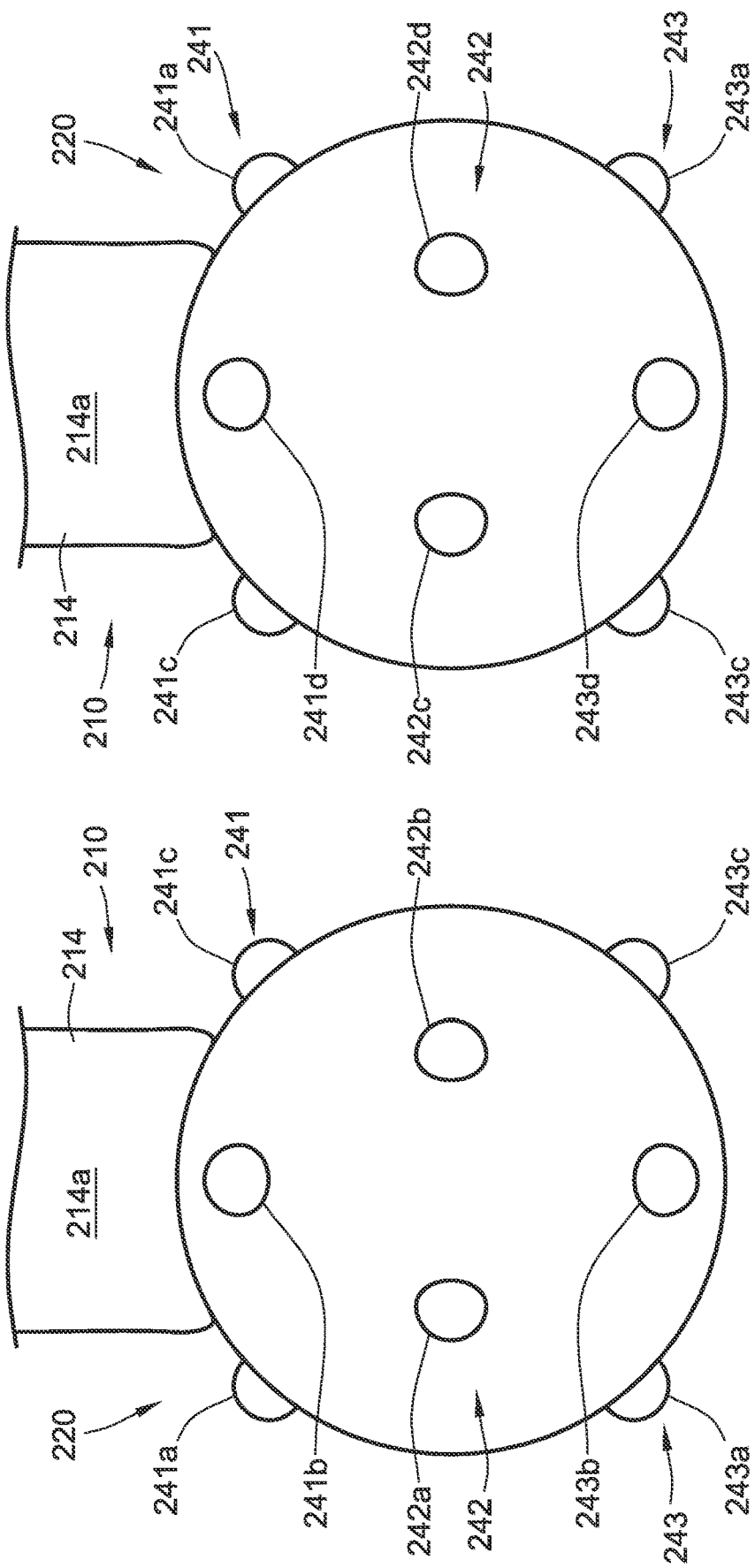

SYSTEMS AND METHODS FOR ESTIMATING A THREE-DIMENSIONAL POSE

CROSS-REFERENCE TO RELATED APPLICATIONS

The present application is a continuation of U.S. patent application Ser. No. 17/012,186, filed Sep. 4, 2020, which is a continuation of U.S. patent application Ser. No. 16/220,117, filed Dec. 14, 2018, now U.S. Pat. No. 10,799,155, which claims priority to U.S. Provisional Patent Application Ser. No. 62/611,112, filed Dec. 28, 2017, the entireties of which are incorporated herein by reference.

FIELD OF THE PRESENT DISCLOSURE

The present disclosure relates generally to motion tracking, and more particularly, to systems and methods for estimating a pose of an oral hygiene device relative to a location.

BACKGROUND

Motion tracking systems are often used in a variety of applications, including, for example, in the medical field, in the movie and video game industries, and the like. There remains a continued need for new systems and methods to accurately track the motion of an object in all directions using a device, such as a smartphone, with limited processing power. The present disclosure addresses these and other problems.

SUMMARY

According to some implementations of the present disclosure, a method for estimating a pose of an oral hygiene device including a pattern and a plurality of groups of visual markers relative to a location the method includes receiving image data reproducible as an image of at least a portion of the oral hygiene device. The method also includes analyzing, using one or more processors, the image data to identify a region of interest within the image, the region of interest including at least a portion of the pattern therein, identifying, using at least one of the one or more processors, all candidate visual markers within the region of interest, and obtaining a first proposed three-dimensional pose of the oral hygiene device. The method further includes validating the first proposed three-dimensional pose of the oral hygiene device, and obtaining a second proposed three-dimensional pose of the oral hygiene device based on the validated first proposed three-dimensional pose.

According to other implementations of the present disclosure, a method for estimating a pose of an oral hygiene device including a pattern and a plurality of groups of visual markers relative to a location includes: (a) receiving image data reproducible as an image of at least a portion of the oral hygiene device; (b) analyzing, using one or more processors, the image data to identify a region of interest within the image, the region of interest including at least a portion of the pattern therein; (c) responsive to identifying the region of interest, segmenting, using at least one of the one or more processors, the region of interest into a plurality of sub-regions, each of the plurality of sub-regions being defined by a plurality of pixels having a common color; (d) identifying, using at least one of the one or more processors, all candidate visual markers within the region of interest; (e) creating a plurality of distinct sets of the candidate visual markers; (f) selecting a first one of the plurality of distinct sets of the candidate visual markers; (g) selecting a first one of a plurality of distinct sets of model markers associated with a three-dimensional model of the oral hygiene device; (h) evaluating the selected set of the candidate visual markers and the selected set of model markers using a perspective-three-point algorithm to obtain a proposed three-dimensional pose of the oral hygiene device; (i) based on the proposed three-dimensional pose of the oral hygiene device, predicting a position within the region of interest for a predetermined number of the candidate visual markers; (j) comparing the predicted positions for the predetermined number of the candidate visual markers with actual positions of all of the candidate visual markers within the region of interest; (k) responsive to a determination that at least a substantial portion of the predicted positions correspond with the actual positions, validating the proposed three-dimensional pose; and (1) responsive to a determination that less than the substantial portion of the predicted positions correspond with the actual positions, repeating steps (f)-(k).

According to other implementations of the present disclosure, a motion tracking system includes an oral hygiene device, a tracking element, a camera, one or more processors, and a memory device. The oral hygiene device includes a head and a handle. The tracking element is coupled to the oral hygiene device and includes a pattern and a plurality of groups of visual markers. The memory device stores instructions that, when executed by at least one of the one or more processors cause the motion tracking system to: capture, using the camera, an image of at least a portion of the oral hygiene device; analyze, using at least one of the one or more processors, the image to identify a region of interest within the image, the region of interest including at least a portion of the pattern of the tracking element therein; identify, using at least one of the one or more processors, all candidate visual markers within the region of interest; create a plurality of distinct sets of the candidate visual markers; select a first one of the plurality of distinct sets of the candidate visual markers; select a first one of a plurality of distinct sets of model markers associated with a three-dimensional model of the oral hygiene device stored in the memory device; evaluate the selected set of the candidate visual markers and the selected set of model markers using a perspective-three-point algorithm to obtain a proposed three-dimensional pose of the oral hygiene device; based on the proposed three-dimensional pose of the oral hygiene device, predict a position within the region of interest for a predetermined number of the candidate visual markers; compare the predicted positions for the predetermined number of the candidate visual markers with actual positions of all of the candidate visual markers within the region of interest; and responsive to a determination that at least a substantial portion of the predicted positions correspond with the actual positions, validate the proposed three-dimensional pose.

According to other implementations of the present disclosure, a motion tracking element configured to be coupled to an oral hygiene device includes a body, a pattern on an outer surface of the body, and a plurality of groups of visual markers on the outer surface of the body.

The above summary of the present disclosure is not intended to represent each embodiment, or every aspect, of the present disclosure. Additional features and benefits of

BRIEF DESCRIPTION OF THE DRAWINGS

FIG. 2B is a front view of the tracking element of FIG. 2A;

FIG. 2C is a rear view of the tracking element of FIG. 2A;

Figure 1:
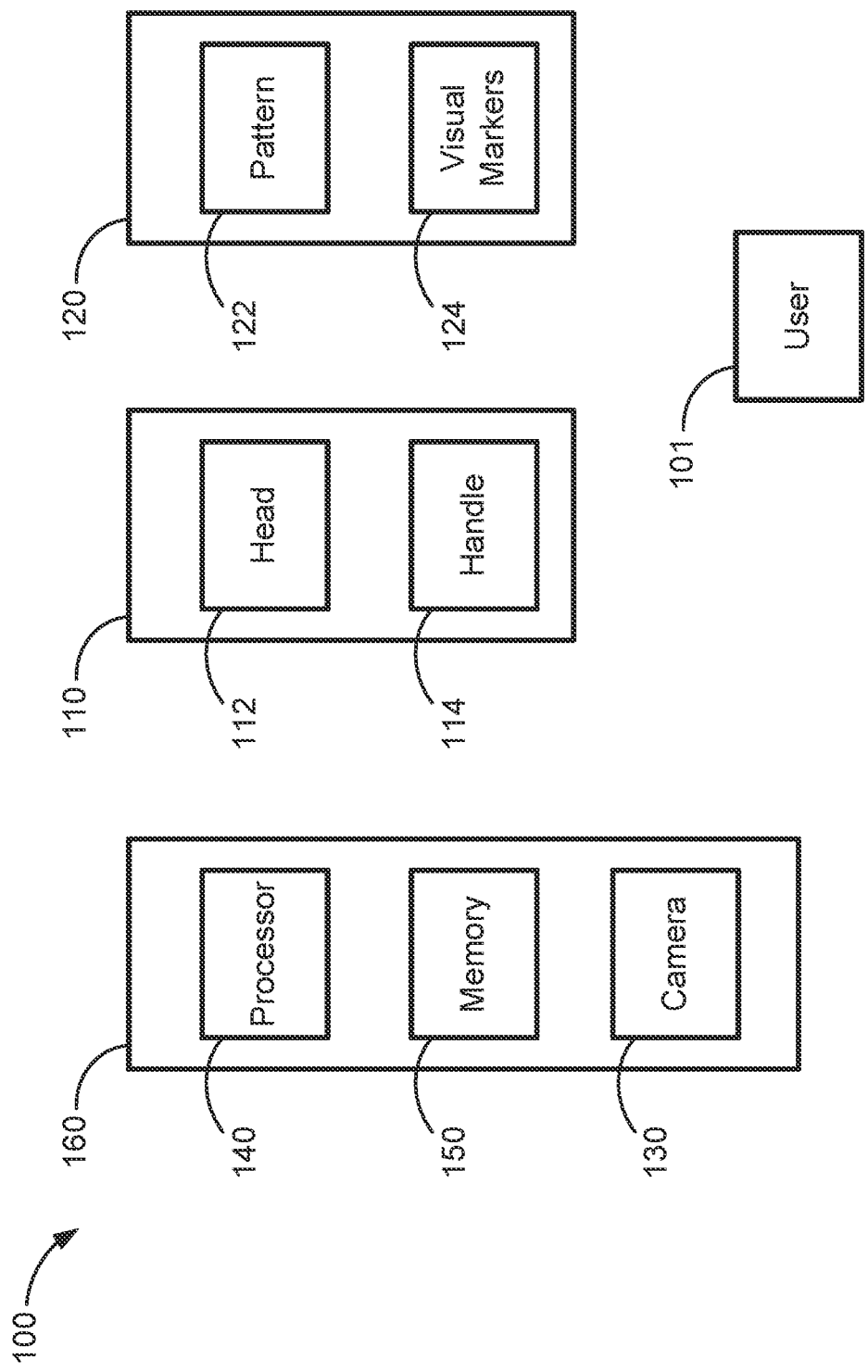
FIG. 1 is a schematic illustration of a motion tracking system according to some implementations of the present disclosure.

While the disclosure is susceptible to various modifications and alternative forms, specific embodiments are shown by way of example in the drawings and are described in detail herein. It should be understood, however, that the disclosure is not intended to be limited to the particular forms disclosed. Rather, the disclosure is to cover all modifications, equivalents and alternatives falling within the spirit and scope of the disclosure.

DETAILED DESCRIPTION

Referring to FIG. 1, a motion tracking system 100 includes an oral hygiene device 110, a tracking element 120, a camera 130, a processor 140, and a memory device 150. The motion tracking system 100 is generally used to estimate a pose of the oral hygiene device 110 in a three-dimensional space relative to a location, such as, for example, the camera 130.

The oral hygiene device 110 includes a head 112 and a handle 114. The head 112 is coupled to a first end of the handle 114 and includes a plurality of bristles for brushing teeth. The head 112 and the handle 114 can be unitary or monolithic or, alternatively, the head 112 can be removably coupled to the handle 114 such that the handle 114 is interchangeable (e.g., with a replacement head). The handle 114 has a generally cylindrical shape, but more generally can be any suitable size and shape. The handle 114 can include an ergonomic grip to aid a user in gripping the handle 114. The oral hygiene device 110 can include an electric motor (not shown) to vibrate and/or oscillate or otherwise provide motion to the head 112 to aid in brushing teeth. More generally, the oral hygiene device 110 can be any manual toothbrush or electric toothbrush.

The tracking element 120 can be detachably coupled (directly or indirectly) to, fixedly or rigidly coupled (directly or indirectly) to, or formed integrally with, the handle 114 of the oral hygiene device 110. Further, the tracking element 120 can be coupled to the handle 114 of the oral hygiene device 110 such that an axis of the tracking element 120 corresponds with or is co-axial with an axis of the handle 114. The tracking element 120 includes a pattern 122 and a plurality of visual markers 124. The tracking element 120 is generally made from a flexible material. For example, the tracking element 120 can be made from a non-conductive material such as, for example, a rubber or elastomer material, a polymer material, or any combination thereof.

The camera 130 is a digital camera that is generally used to capture still images, video images, or both, of at least a portion of the oral hygiene device 110 and the tracking element 120. Typically, the oral hygiene device 110 is positioned between the user 101 and the camera 130 such that the field of view of the camera 130 encompasses at least a portion of the oral hygiene device 110 and at least a portion of the tracking element 120.

The processor 140 is communicatively coupled to the camera 130 and the memory device 150. The processor 140 executes instructions (e.g., an associated application) stored in the memory device 150 to control the various components of the system 100 to which it is communicatively coupled.

In some implementations, the system 100 further includes a housing 160. In such implementations, the camera 130, the processor 140, the memory device 150, or any combination thereof can be integrated in the housing 160. For example, the housing 160 can be a smartphone. Alternatively, some or all of the various components can be decoupled from one another, and some can be included in a base station (not shown) for the oral hygiene device 110.

Figure 2A:
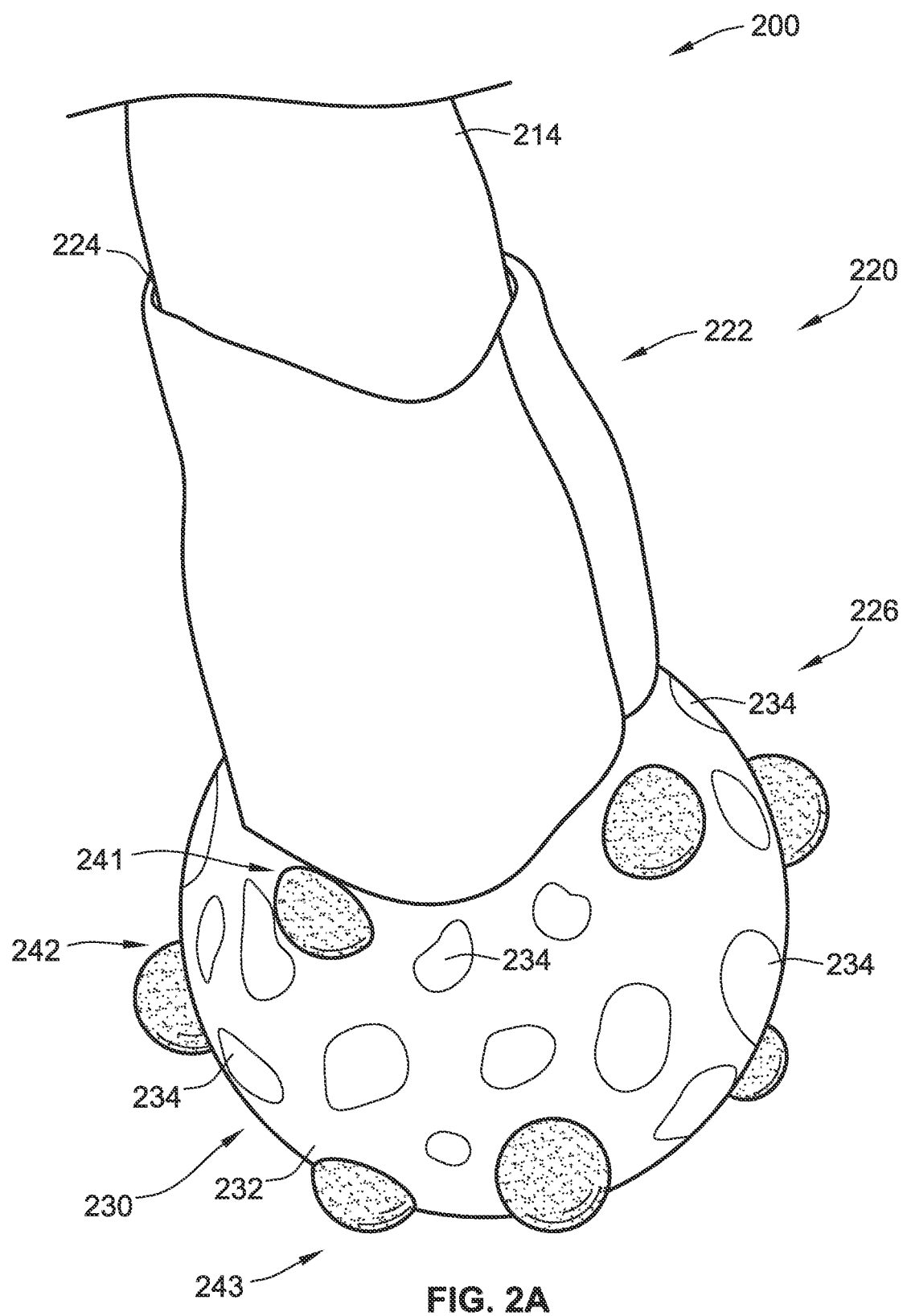
FIG. 2A is a perspective view of a tracking element and an oral hygiene device according to some implementations of the present disclosure.

Referring to FIGS. 2A-2C, an oral hygiene device 210 that is the same as or similar to the oral hygiene device 110 is coupled to a tracking element 220 that is the same as or similar to the tracking element 120 described above.

The oral hygiene device 210 includes a head (not shown) and a handle 214. The head is a coupled to a first end of the handle 214 and the tracking element 220 is coupled to a second end of the handle 214 that is opposite the head.

The tracking element 220 includes an upper portion 222, a lower portion 226, a pattern 230, a first group of visual markers 241, a second group of visual markers 242, and a third group of visual markers 243. The upper portion 222 has a generally cylindrical configuration and includes a cavity 224. The cavity 224 is sized and shaped to receive the handle 214 of the oral hygiene device 210 therein to removably couple the tracking element 220 to the handle 214 using a press or interference fit. The upper portion 222 may, for example, be formed from an elastomeric material in the form of a sleeve and be configured and arranged to receive and conform to the second end of the handle 214. Alternatively, the tracking element 220 can be coupled to the handle 214 using other mechanisms, such as, for example, a threaded connection, an adhesive connection, a hook and loop fastener, a tab and aperture system, a press or interference fit connection, a snap fit connection, a force fit connection, a twist-lock connection, or the like, or any combination thereof. Alternatively, in some implementations, the tracking element 220 includes a male attachment feature and the second end of the handle 214 can include a cavity that is similar to the cavity 224 and is sized and shaped to receive at least a portion of the male attachment feature therein. In such implementations, the tracking element 220 male attachment feature and the cavity of the handle 214 can be coupled using any of the fastening mechanisms described above. Advantageously, in this configuration, the tracking element 220 can be removed from the oral hygiene device 210 if the user does not desire to use the tracking element 220 during a given brushing session. Further, the tracking element 220 can be removed from the oral hygiene device 210 and coupled to a second oral hygiene device such as, for example, when the user replaces the oral hygiene device 210 at the end of its useful life or in the event another user desires to use the tracking element 220 on another oral hygiene device. Alternatively, the tracking element 220 and the handle 214 can be unitary and/or monolithic.

As shown in FIGS. 2A-2C, the lower portion 226 of the tracking element 220 can have a generally spherical configuration, although other sizes and shapes are possible. As shown, the pattern 230 formed on an outer surface thereof and is flush with the outer surface of the lower portion 226 and includes a background 232 and a plurality of indicators 234.

As shown, each of the plurality of indicators 234 have an amorphous shape that is generally circular-like or oval-like. The shape of the plurality of indicators 234 shown in FIG. 2A-2C is preferable because this shape minimizes blur associated with movement of the oral hygiene device 210 and the tracking element 220 when capturing an image of the same. Alternatively, one or more of the indicators of the plurality of indicators 234 can have a generally triangular shape, a generally rectangular shape, a polygonal shape, or any combination thereof. While each of the plurality of indicators 234 is shown as having the same shape and size, each of the plurality of indicators 234 can have a different size or substantially the same size (e.g., diameter).

Each of the plurality of indicators 234 have a first color and the background 232 has a second color that is different than the first color. In one example, the background 232 is an orange color and each of the plurality of indicators 234 are a black color. Alternatively, the background 232 can be a black color and each of the plurality of indicators 234 can be a generally orange color, although other colors for the background 232 and the plurality of indicators 234 are possible (e.g., red, green, blue, yellow, orange, purple, etc.). In general, a high contrast between the color of the background 232 and each of the plurality of indicators 234 is preferable so as to clearly define each of the plurality of indicators 234. The plurality of indicators 234 defining the pattern 230 on the tracking element 220 can have between about ten indicators and about one hundred indicators, between about twenty indicators and about sixty indicators, between about thirty-five and about forty-five indicators, or any suitable number of indicators.

The plurality of indicators 234 and the background 232 of the pattern 230 can be formed using a variety of mechanisms. For example, at least some of the plurality of indicators 234 and/or the background 232 of the pattern 230 can be printed or embossed on the outer surface of the tracking element 220. Alternatively, at least some of the plurality of indicators 234 and/or the background 232 can be integral with the lower portion 226.

Referring to FIGS. 2A-2C, the first group of visual markers 241, the second group of visual markers 242, and the third group of visual markers 243 are coupled to the outer surface of the lower portion 226 and protrude therefrom. As shown, each visual marker in the groups of visual markers 241, 242, 243 has a generally ovoid, dome-like or semi-spherical shape. The first, second, and third groups of visual markers 241, 242, 243 can be coupled to the outer surface of the lower portion 226 using an adhesive connection, for example, or more generally any other suitable mechanism. Alternatively, each of the visual markers can be unitary and/or monolithic with the lower portion 226 of the tracking element 220.

Referring to FIGS. 2B and 2C, the first group of visual markers 241 includes a first visual marker 241a, a second visual marker 241b, a third visual marker 241c, and a fourth visual marker 241d. The handle 214 has a front surface 214a and a rear surface 214b. The cleaning elements (e.g., bristles) on the head (not shown) extend from the front surface 214a of the handle 214. To illustrate all of the visual markers, FIG. 2B is a front view of the oral hygiene device 210 (i.e., includes the front surface 214a) and FIG. 2C is a rear view the oral hygiene device 210 (i.e., includes the rear surface 214b).

In some implementations, the first group of visual markers 241 extends along a first circumferential length of the lower portion 226 that is proximate to the upper portion 222 and the handle 214. As shown, each of the visual markers in the first group of visual markers 241 are evenly spaced from one another along the first circumferential length.

The second group of visual markers 242 includes a first visual marker 242a, a second visual marker 242b, a third visual marker 242c, and a fourth visual marker 242d. The second group of visual markers 242 extends along a second circumferential length of the lower portion 226 that is spaced from the first circumferential length. As shown, each of the visual markers in the second group of visual markers 242 are evenly spaced from one another along the first circumferential length, but offset circumferentially from the visual markers in the first group of visual markers 241. Specifically, the first visual marker 242a is positioned between the first visual marker 241a and the second visual marker 241b of the first group of visual markers 241 (FIG. 2B), the second visual marker 242b is positioned between the second visual marker 241b and the third visual marker 241c of the first group of visual markers 241 (FIG. 2B), the third visual marker 242c is positioned between the third visual marker 241c and the fourth visual marker 241d of the first group of visual markers 241 (FIG. 2C), and the fourth visual marker 242d is positioned between the fourth visual marker 241d and the first visual marker 241a of the first group of visual markers 241 (FIG. 2D).

The third group of visual markers 243 includes a first visual marker 243a, a second visual marker 243b, a third visual marker 243c, and a fourth visual marker 243d. The third group of visual markers 243 extends along a third circumferential length of the lower portion 226 that is spaced from the second circumferential length and distal to the upper portion 222 and the handle 214. The first circumferential length, the second circumferential length, and the third circumferential length are evenly spaced from one another such that the first group of visual markers 241, the second group of visual markers 242, and the third group of visual markers 243 are evenly spaced from one another.

The third group of visual markers 243 includes a first visual marker 243a, a second visual marker 243b, a third visual marker 243c, and a fourth visual marker 243d. The first visual marker 243a is aligned with the first visual marker 241a of the first group of visual markers 241 such that the first visual marker 243a is positioned between the fourth visual marker 242d and the first visual marker 242a of the second group of visual markers 242. The second visual marker 243b is aligned with the second visual marker 241b of the first group of visual markers 241 such that the second visual marker 243b is positioned between the first visual marker 242a and the second visual marker 242b of the second group of visual markers 242. The third visual marker 243c is aligned with the third visual marker 241c of the first group of visual markers 241 such that the third visual marker 243c is positioned between the second visual marker 242b and the third visual marker 242c of the second group of visual markers 242. The fourth visual marker 243d is aligned with the fourth visual marker 241d of the first group of visual markers 241 such that the fourth visual marker 243d is positioned between the third visual marker 242c and the fourth visual marker 242d of the second group of visual markers 242.

Each of the visual markers within the first group of visual markers 241, the second group of visual markers 242, and the third group of visual markers 243 has a distinctive color. For example, in the first group of visual markers 241, the first visual marker 241a has a first color, the second visual marker 241b has a second color, the third visual marker 241c has a third color, and the fourth visual marker 241d has a fourth color. The first color, the second color, the third color, and the fourth color are all different from one another. Preferably, the first color, second color, third color, and fourth color are separate and distinct colors that are spaced out along the color spectrum. For example, each color can be spaced from the other colors by between about a 150 nm wavelength to a 15 nm wavelength in the color spectrum, about a 100 nm wavelength in the color spectrum to about a 25 nm wavelength in the color spectrum, or about a 75 nm wavelength in the color spectrum to about a 50 nm wavelength in the color spectrum, or the like. For example, the first color, second color, third color, and fourth color can be a blue color, a green color, a purple color, a yellow color, a red color, or an orange color, which are spread out substantially equally along the color spectrum.

In one example, referring to the first group of visual markers 241, the first visual marker 241a is a purple color, the second visual marker 241b is a blue color, the third visual marker 241c is a yellow color, and the fourth visual marker 241d is a green color. Referring to the second group of visual markers 242, the first visual marker 242a is a yellow color, the second visual marker 242b is a green color, the third visual marker 241c is a blue color, and the fourth visual marker 241d is a purple color. Referring to the third group of visual markers 243, the first visual marker 243a is a green color, the second visual marker 243b is a purple color, the third visual marker 243c is a blue color, and the fourth visual marker 243d is a yellow color. In this configuration, each of the four colors (blue, green, purple, and yellow) are evenly distributed and spaced from one another among the groups of visual markers. For example, a yellow visual marker is not directly adjacent to another yellow visual marker and a blue visual marker is not directly adjacent to another blue visual marker.

In this example described above, there are three purple visual markers, three blue visual markers, three yellow visual markers, and three green visual markers (i.e., markers with four different colors). While each of the first group of visual markers 241, the second group of visual markers 242, and the third group of visual markers 243 is shown as including four visual markers, more generally, the attachment 220 can include any number of groups of visual markers including at least one visual marker. For example, the attachment 220 can include a first group of visual markers, a second group of visual markers, a third group of visual markers, and a fourth group of visual markers, with each group containing at least one visual marker. Further, the at least one visual marker in each group has a different color than the visual markers in the other groups. Further, while the attachment 220 (FIGS. 2A-2B) is shown as including twelve visual markers combined between the first group 241, the second group 242, and the third group 243, it should be understood that the attachment 220 can include any number of visual markers (e.g., four visual markers, six visual markers, ten visual markers, twenty visual markers, fifty visual markers, etc.) having four or more different colors (e.g., four different colors, six different colors, ten different colors, twenty different colors, etc.). As will be discussed in more detail herein, having four or more visual markers having different colors is preferable to accurately and efficiently track motion of the tracking element 220. Further, while the first group of visual markers 241, the second group of visual markers 242, and the third group of visual markers 243 are each positioned along a circumferential length of the lower portion 226 and are evenly spaced from one another, the visual markers can be positioned relative to one another in any appropriate arrangement (e.g., randomly) on the outer surface of the lower portion 226.

Figure 3:
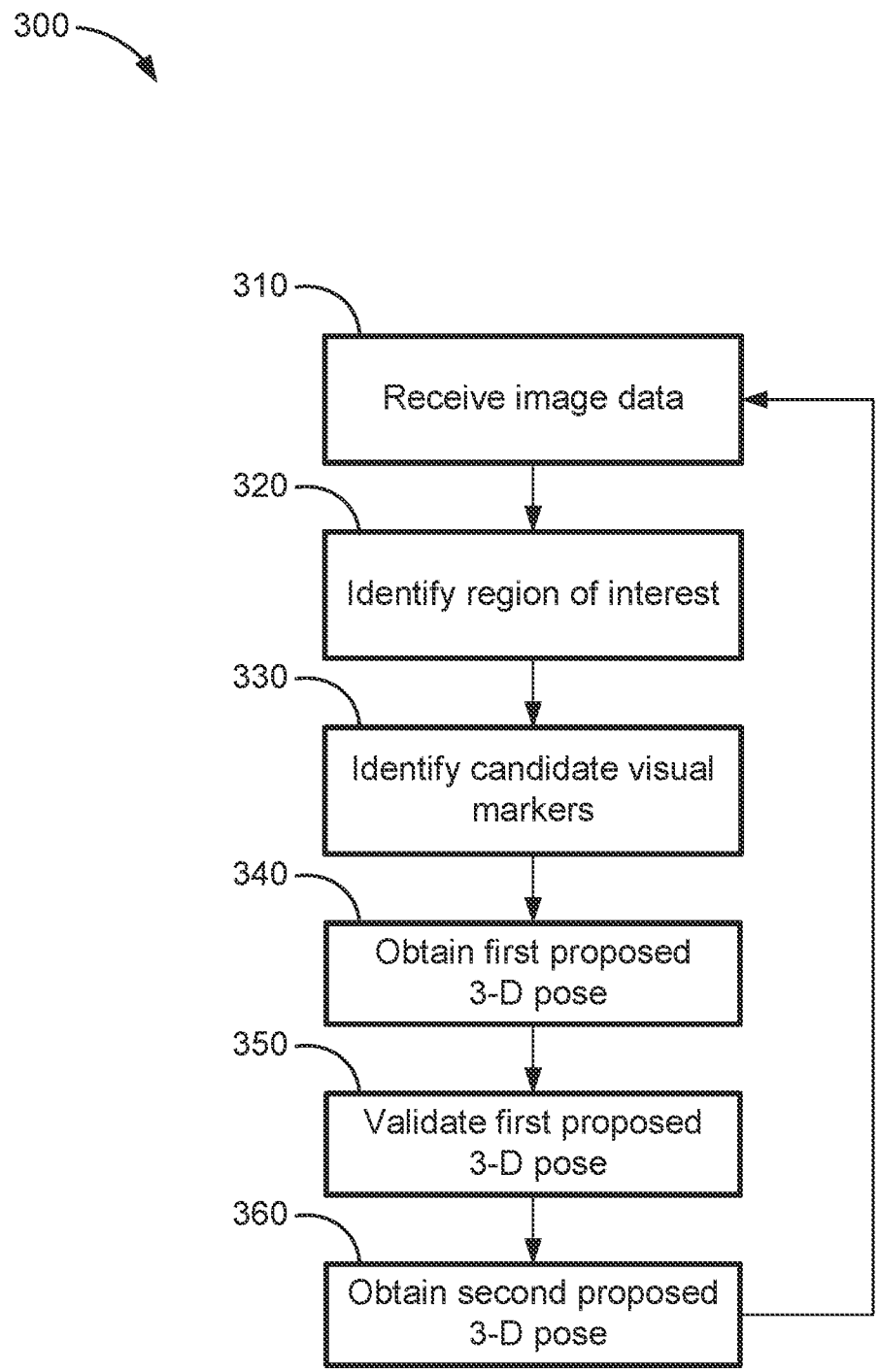
FIG. 3 is a flow diagram for a method for estimating a pose of an oral hygiene device relative to a location according to some implementations of the present disclosure.

Referring to FIG. 3, a method 300 for estimating a pose of the oral hygiene device 210 relative to a location includes, for example, a first step 310, a second step 320, a third step 330, a fourth step 340, a fifth step 350, and a sixth step 360.

The first step 310 includes receiving image data, from a camera that is the same as or similar to the camera 130 (FIG. 1) described above, that is reproducible as an image of at least a portion of the oral hygiene device 210 and at least a portion of the tracking element 220. For example, the image data can be a frame of a video image captured by the camera. As described above, the camera is positioned relative to the user (e.g., user 101) such that the oral hygiene device 210 and the tracking element 220 are positioned between the camera and the user. Because the field of view of the camera encompasses the oral hygiene device 210, the tracking element 220, and at least a portion of the user, the captured video or still image includes at least a portion of all three and the background behind the user that is within the field of view of the camera.

The second step 320 includes analyzing the image data from the first step 310 to identify a region of interest within the image. Generally, the region of interest is an area of the image received during the first step 310 that includes the tracking element 220. As described above, the image captured during the first step 310 includes at least a portion of the user and a background behind the user. By limiting the region of interest to an area surrounding the tracking element 220, the processing requirements for the subsequent steps of the method 300 can be reduced.

To analyze the image data and identify the region of interest, one or more processors that are the same as or similar to the processor 140 (FIG. 1) described above are used to identify the pattern 230 of the tracking element 220 (FIG. 2A) using a plurality of filters. The plurality of filters includes a movement filter, a color filter, and a shape filter. The movement filter detects or identifies movement within the image. Generally, the movement filter detects movement by distinguishing areas of movement in the image compared to stationary areas of the image. The movement filter takes advantage of the fact that the pattern 230 is likely to be moving due to corresponding movement of the oral hygiene device 210 and the tracking element 220 to narrow the potential area(s) of the image that could be the region of interest (i.e., contain at least a portion of the pattern 230) by eliminating the stationary background of the image. The color filter and the shape filter identify the contrast in color between the background 232 and the plurality of indicators 234 and the shape of each of the plurality of indicators 234. Having detected an area of the image containing the pattern 230, the region of interest is defined as that area and excludes the remainder of the image.

Identifying the region of interest in a high resolution or high definition image requires substantial processing/computation time. To reduce the processing requirements for identifying the region of interest, the image analyzed during the second step 320 is preferably a low resolution image. The region of interest can then be upscaled to a higher resolution image for the remainder of the steps of the method 300.

In some implementations, the pattern 230 of the tracking element 220 can be filtered or detected to identify the region of interest using a machine learning algorithm or an artificial intelligence algorithm. Machine learning algorithms may take a variety of forms. For example, the method 300 can utilize more basic machine learning tools such as a decision tree ("DT") or an artificial neural network ("ANN"). DT programs are generally used because of their simplicity and ease of understanding. DT are classification graphs that match input data to questions asked at each consecutive step in a decision tree. The DT program moves down the "branches" of the tree based on the answers to the questions. For example, a first branch may ask if a portion of the image is moving. If yes, a second branch may ask whether the portion of the image includes the pattern 230. In other examples, deep learning algorithms or other more sophisticated machine learning algorithms can be used, such as, for example, a convolutional neural network.

Machine learning algorithms (e.g., a Haar Cascade) require training data to identify the features of interest that they are designed to detect. For instance, various methods may be utilized to form the machine learning models including applying randomly assigned initial weights for the network and applying gradient descent using back propagation for deep learning algorithms. In other examples, a neural network with one or two hidden layers can be used without training using this technique. In some examples, the machine learning algorithms will be trained using labeled data, or data that represents certain features, specific actions, or characteristics, including a particular color or a particular shape.

The third step 330 includes identifying candidate visual markers in the region of interest identified during the second step 320. Generally, candidate visual markers are sub-regions of the region of interest that could be an actual visual marker (e.g., one of the visual markers of the groups of visual markers 241, 242, or 243 in FIGS. 2A-2C) on the tracking element 220. To identify candidate visual markers, the region of interest is segmented in a plurality of sub-regions using a color segmentation algorithm. Each sub-region is defined by a plurality of pixels of the region of interest that have a common color.

Generally, the color segmenting algorithm assumes that objects are colored distinctively and seeks to identify gross color differences between adjacent pixels in an image. The color segmenting algorithm uses the L*a*b color space, which defines colors in terms of luminosity ("L"), where the color falls along the red-green axis ("*a"), and where the color falls along the blue-yellow axis ("*b"). As a result, if necessary, the region of interest identified in the second step 320 is converted from a RGB color space to the L*a*b color space to perform the color segmenting algorithm. Using a threshold value, the color segmenting algorithm separates adjacent pixels having distinctive colors from one another to form a plurality of sub-regions. The average color in the L*a*b color space of each of the plurality of sub-regions is then calculated.

As discussed above, the color of the visual markers in the first group 241, the second group 242, and the third group 243 preferably is one of blue, green, purple, yellow color, red, or orange. Thus, a sub-region of the region of interest having a blue, green, purple, or yellow color could be a candidate visual marker. While the region of interest is limited to an area encompassing the tracking element 220, the region of interest may still include a portion of the user or the background behind the user, which can create false positive for a candidate visual marker. For example, the user may be wearing clothing which has one or more of the same or similar colors as the visual markers.

To increase the accuracy of identifying candidate visual markers, the third step 330 also includes a shape filter and a size filter. The visual markers of the first group of visual markers 241, the second group of visual markers 242, and the third group of visual markers 243 (FIGS. 2A-2C) have a generally dome-like or hemispheric shape. When viewed in a two-dimensional image such as the region of interest, these visual markers have a generally circular shape. The shape filter and the size filter are used to detect the generally circular shape of the visual markers within the region of interest. These filters aid in discriminating between a visual marker and, for example, the clothing of the user.

The fourth step 340 includes obtaining a first proposed three-dimensional pose of the oral hygiene device 210. Generally, the first proposed three-dimensional pose includes the position and orientation (rotation and translation) of the oral hygiene device 210 relative to the camera. As will be discussed in more detail herein, in some implementations, the fourth step 340 will not initialize until at least four candidate visual markers are identified during the third step 330. If less than four candidate visual markers are identified during the third step 330, the method 300 is repeated until at least four candidate visual markers are identified.

Figure 4:
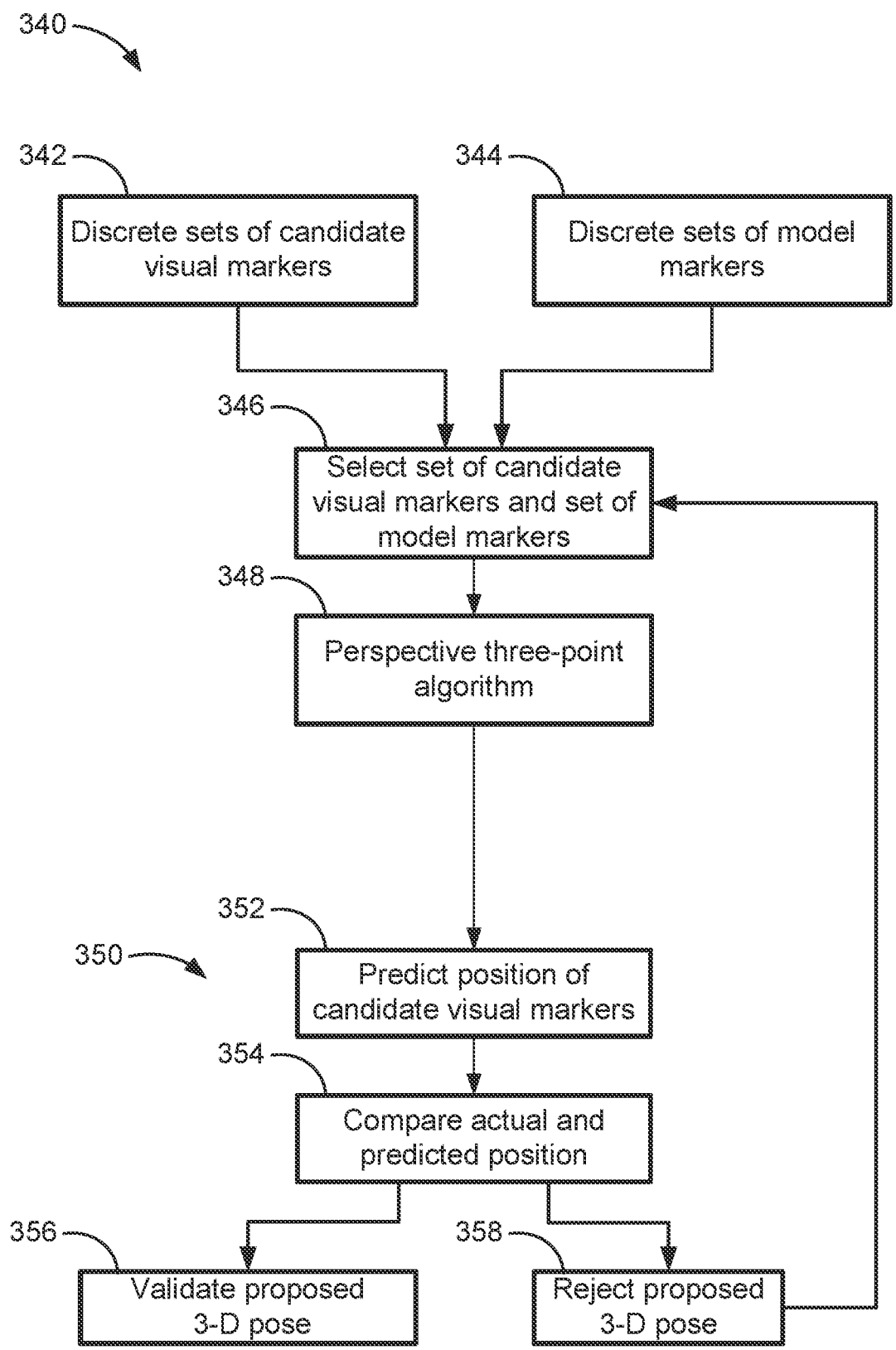
FIG. 4 is a flow diagram illustrating of a step of obtaining a first proposed three-dimensional pose and a step of validating the first proposed three-dimensional pose.

Referring to FIG. 4, the fourth step 340 includes a first sub-step 342, a second sub-step 348, a third sub-step 348, and a fourth sub-step 348.

The first sub-step 342 includes grouping the candidate visual markers identified during the third step 330 (FIG. 3) into discrete sets of candidate visual markers. Preferably, each of the discrete sets of candidate visual markers includes four candidate visual markers.

Similarly, the second sub-step 348 includes grouping model markers from a three-dimensional model of the oral hygiene device 210 and the tracking element 220 into discrete steps. The three-dimensional model is stored in a memory device that is the same as or similar to the memory device 150 described above (FIG. 1). The three-dimensional model is a representation of the actual oral hygiene device 210 and the tracking element 220. Specifically, the three-dimensional model includes representations of the first group of visual markers 241, the second group of visual markers 242, and the third group of visual markers 243. The number of model markers in each of the discrete sets of model markers is equal to the number of candidate visual markers in the first discrete set of candidate visual markers grouped together during the first step 342 (e.g., four candidate visual markers and four model markers).

The third sub-step 348 includes selecting a first discrete set of candidate visual markers and a first discrete set of model markers. The first discrete set of candidate visual markers includes four visual markers and the first discrete set of model markers includes four model markers.

The fourth sub-step 348 includes inputting the first discrete set of candidate visual markers and the first discrete set of model markers selected during the third sub-step 348 into a perspective-three-point ("P3P") algorithm. The P3P algorithm is based on the law of cosines and is used to estimate an object pose (a rotation and translation) relative to the camera placement.

Generally, the P3P algorithm compares two-dimensional points taken from an image with three-dimensional points taken from a three-dimensional model. To solve the P3P equation system, four two-dimensional points defined in an image coordinate system and four three-dimensional points defined in a three-dimensional model coordinate system are provided. Three sets of points, each set including a two-dimensional point and a three-dimensional point, are used to solve the P3P equation system and determine up to four possible sets of distances between the two-dimensional points and the optical center of the camera. These four sets of distances are converted into four pose configurations. The fourth set of 2D/3D points is then used to select the best or most correct pose configuration against the four proposals. There are various methods for solving the P3P equation system and obtaining an estimated three-dimensional pose. For example, one such method is explained in Laurent Kneip et. al, A Novel Parametrization of the Perspective-Three-Point Problem for a Direct Computation of Absolute Camera Position and Orientation, The IEEE Conference on Computer Vision and Pattern Recognition (CVPR), June 2011), which is hereby incorporated by reference in its entirety.

Inputting the first discrete set of candidate visual markers and the first discrete set of model markers into the P3P algorithm and solving the equation system yields a first proposed three-dimensional pose of the oral hygiene device 210. The first proposed three-dimensional pose includes a rotational and a translational position of the oral hygiene device 210 that permits the position of the oral hygiene device 210 relative to the camera to be determined. As discussed above, in some implementations, the fourth step 340 will not initialize until four candidate visual markers are identified during the third step 330. This is because solving the P3P algorithm requires four candidate visual markers and four model markers. If less than four candidate visual markers are identified in the third step 330, the P3P algorithm equation system generally cannot be solved without more data.

The fifth step 350 (FIG. 3) includes validating the first proposed three-dimensional pose of the oral hygiene device 210 determined during the fourth step 340. It is possible that the first discrete set of candidate visual markers and the first discrete set of model markers selected in sub-step 348 yield a proposed three-dimensional pose that is incorrect (e.g., a pose that is not physically possible). Thus, the fifth step 350 is generally used to validate or reject the proposed three-dimensional pose obtained during the fourth step 340.

Referring to FIG. 4, the fifth step 350 includes a first sub-step 352, a second sub-step 354, a third sub-step 356, and a fourth sub-step 358. The first sub-step 352 includes predicting the positions of the candidate visual markers within the region of interest. Based on the first proposed three-dimensional pose calculated during the fourth step 340, and the known positions of visual markers from the three-dimensional model of the oral hygiene device 210 and the tracking element 220, the position of the visual markers within the region of interest can be predicted. In other words, the predicted positions indicate where candidate visual markers should be located in the region of interest if the first proposed three-dimensional pose is correct, and where candidate visual markers should not be located. For example, it may be predicted that six visual markers will be visible in the region of interest if the oral hygiene device 210 has the same pose as the first proposed three-dimensional pose. The position of these six visual markers relative to one another in the region of interest is determined from the three-dimensional model of the oral hygiene device.

The second sub-step 354 includes comparing the candidate visual markers identified in the region of interest with the predicted positions of the visual markers. More specifically, the number and position of the candidate visual markers is compared to the predicted number and predicted position of the visual markers (first sub-step 354 of the fifth step 350). If it is determined that the positions of a predetermined number of the candidate visual markers correspond to the predicted positions, the first proposed three-dimensional pose is validated (sub-step 356). If less than the predetermined number of candidate markers correspond to the predicted positions, the first proposed three-dimensional pose is rejected (sub-step 358).

To illustrate by way of an example, the first sub-step 352 predicts that six candidate visual markers will be visible in the region of interest, and predicts the position of each of these six candidate visual markers relative to one another. The third step 330 identified ten candidate visual markers within the region of interest. If, for example, a candidate visual marker corresponds to five of the six predicted visual markers, the first proposed three-dimensional pose is validated (sub-step 356) and the fifth step 350 is completed. The other four candidate visual markers are simply considered to be noise or inaccurate. Alternatively, if there are thirty candidate visual markers identified during the third step 330, and for example, twenty-five of the thirty do not correspond to a predicted position, the proposed three-dimensional pose may be rejected.

The predetermined number of correspondences required to validate a proposed three-dimensional pose can be expressed as a percentage, and can be at least about 50% of the predicted positions of the visual markers correspond to positions of candidate visual markers, at least about 60% of the predicted positions of the visual markers correspond to positions of candidate visual markers, at least about 70% of the predicted positions of the visual markers correspond to position of candidate visual markers, at least about 80% of the predicted positions of the visual markers correspond to positions of candidate visual markers, at least about 90% of the predicted positions of the visual markers correspond to positions of candidate visual markers, or 100% of the predicted positions of the visual markers correspond to positions of candidate visual markers). In some implementations, the predetermined number is a statistically significant number such that it can be determined that the first proposed three-dimensional pose is correct with a suitable statistical certainty (e.g., 95% statistical certainty, 85% statistical certainty, 75% statistical certainty, etc.).

If the first proposed-three dimensional pose is rejected (sub-step 358), the second sub-step 348 (FIG. 4) of the fourth step 340 is repeated. During the repeating of the sub-step 348, a second discrete set of candidate visual markers and a second discrete set of model markers are selected. At least one of the second discrete set of candidate visual markers and the second discrete set of models markers includes a set of candidate visual markers or model markers that is different from the first discrete set of candidate visual markers and/or the second discrete set of model markers. These sets are then inputted into the P3P algorithm in sub-step 348 to obtain a second proposed three-dimensional pose of the oral hygiene device 210. The second proposed three-dimensional pose is then validated or rejected during the fifth step 350. Steps 348 through 354 are repeated until a proposed three-dimensional pose is validated (sub-step 356).

During the repeating of the steps described above to validate a proposed three-dimensional pose, numerous discrete sets of candidate visual markers and discrete sets of model markers may be inputted into the P3P algorithm until a proposed pose is validated. Because there are twelve visual markers collectively between the first group of visual markers 241 in the example shown in FIGS. 2A-2C, the second group of visual markers 242, and the third group of visual markers 243 (FIGS. 2A-2C), there are 469 possible combinations of four visual markers if the color of the visual markers is disregarded. In other words, there are 469 possible discrete sets of four model markers. If for example, there are sixteen candidate visual markers identified in the region of interest (during step 330), disregarding color, there are 1,820 combinations of four candidate visual markers (i.e., 1,820 possible discrete sets of candidate visual markers). This means that there is potentially over 900,000 proposed three-dimensional poses that may be determined before one is validated, requiring substantial processing/computation time. However, as described above, each of the first group of visual markers 241, the second group of visual markers 242, and the third group of visual markers 243 includes four visual markers, and each of the four visual markers in each group has a different color. The grouping of candidate visual markers and model markers can then be further conditioned such that each group not only is limited to four visual markers, but each visual marker in the group of four has a different color. In this manner, the number of possible combinations that may need to be inputted into the P3P algorithm (sub-step 348) before validating a proposed three-dimensional pose (sub-step 356) is reduced from, for example, the hundreds of thousands to several hundred. This reduces the processing/computational requirements such that the method can be implemented on, for example, a smartphone with limited processing power.

The sixth step 360 includes obtaining a second proposed three-dimensional pose of the oral hygiene device 210 based on the validated first proposed three-dimensional pose of the oral hygiene device 210. The second proposed three-dimensional pose of the oral hygiene device 210 is calculated in a similar manner as the first proposed three-dimensional pose during the fifth step 350. As discussed above, during the first sub-step 352 of the fifth step 350, the positions of each of the visual markers in the region of interest are predicted. As also discussed above, there may be a greater number of candidate visual markers identified during the third step 330 than the amount of predicted visual markers due to noise from the background or inaccuracy involved in the color segmenting algorithm. To obtain a more refined pose estimation, the sixth step 360 selects only the candidate visual markers ("correct candidate visual markers") that correspond to predicted visual markers, ignoring candidate visual markers that are incorrect based on the predicted positions. These correct candidate visual markers are then compared to model markers from the three-dimensional model of the oral hygiene device 210 using an iterative pose estimation algorithm and linear regressions to obtain a second proposed three-dimensional pose of the oral hygiene device 210. The second proposed three-dimensional pose of the oral hygiene device 210 is generally more accurate than the first proposed three dimensional pose (fourth step 340), but requires more processing/computation time to determine.

Referring to FIG. 3, after completion of the sixth step 360, the method 300 can be repeated one or more times. In a second iteration of the method 300, the first step 310 is repeated and includes receiving image data that is reproducible as a second image of at least a portion of the oral hygiene device 210 and the tracking element 220. For example, the second image can be a second frame of a video image that is taken subsequent to the image used during the initial iteration of the method 300.

The second step 320 is then repeated to identify a second region of interest in the second image received during the first step 310. However, in the second iteration of the method 300, detection of the pattern 230 of the tracking element 220 to identify the region of interest is bypassed. Instead the second region of interest is selected using the second three-dimensional pose estimation (sixth step 360), and the second region of interest is defined an area of the second image in which at least a portion of the tracking element 220 is positioned. Because the second step 320 in the second iteration of the method 300 does not require detection of the pattern 230 using a plurality of filters, the required processing/computation time to complete the second step 320 is reduced.

The third step 330 is then repeated to identify all of the candidate visual markers in the second region of interest using the color segmenting algorithm described above. Typically, the oral hygiene device 210 will be used in a bathroom that may have bright or intense lighting, which can be further amplified by reflections in a bathroom mirror. Further, movement of the oral hygiene device 210 may cause the lighting conditions in the region of interest to change based on position of the oral hygiene device relative to a light source (e.g., the user may cast a shadow on a portion of the oral hygiene device 210 in a particular pose). The lighting conditions and/or movement of the oral hygiene device 210 may affect the amount of light reflecting off of the visual markers of the tracking element 220. For example, it may be difficult to discern a blue color from a purple under intense or bright lighting conditions or dark lighting conditions. By using the second three-dimensional pose estimation obtained during the sixth step 360, the threshold for distinguishing colors in the color segmenting algorithm can be adjusted based on the three-dimensional pose estimation obtained in the sixth step 360 of the first iteration of the method 300. This threshold is then updated each time the third step 330 is completed as the method 300 is repeated.

The fourth step 340, the fifth step 350, and the sixth step 360 are then repeated in the same or similar manner as described above to obtain another second three-dimensional pose estimation of the oral hygiene device 210.

Steps 310 through 360 can then be repeated a plurality of times (e.g., ten times, fifty times, one hundred times, one thousand times, etc.) after the second iteration described above description to track motion of the oral hygiene device 210. The sixth step 360 will output a series of estimated three-dimensional poses of the oral hygiene device 210 as the method 300 is repeated, which can be then used to track the movement of the oral hygiene device 210 over time. This repeating of the method 300 can be used to track the motion of the oral hygiene device 210 during, for example, a brushing session in which a user is brushing their teeth. Data relevant to the quality of brushing by a user or the overall dental health of the user's teeth can be collected and analyzed based on the motion data. For example, a brush stroke type (e.g., a side-to-side stroke, an angular stroke, or a circular stroke) can be determined.

In some implementations, the system 100 can also be utilized to determine the position and orientation of a face of a user. For example, using the camera 104, the system 100 receives an image of at least a portion of the face of the user. Using the processor 140 and the memory 150 and a facial recognition algorithm, the position and orientation of the face can be determined. For example, the system 100 may determine the position of the user's eyes, mouth, or nose (or any combination thereof) using, for example, a plurality of filters, machine-learning algorithms, or the like. In one example, the position of the user's mouth can be estimated based on the position of the user's eyes and a distance between the eyes and mouth of the user.

By determining the position and orientation of the face of the user, the position of the oral hygiene device 210 can be determined not only with respect to the camera, but to the mouth of the user. Thus, the position of the oral hygiene device relative to the teeth of the user and thus determine and whether a user has a brushed a certain section of teeth can be determined.

In some implementations, the method 300 further includes an initial calibration step to determine the rotational position of the tracking element 220 relative to the oral hygiene device 210. For example, using the techniques described above, the calibration step can initially determine the rotational position of the tracking element 220 on the oral hygiene device 210 and communicate that position to adjust the three-dimensional model so that the rotational position of the tracking element 220 in the three-dimensional model corresponds with the rotational position on the actual oral hygiene device 210. In other implementations, the method 300 is agnostic to how the tracking element 220 is coupled to the handle 214 of the oral hygiene device 210.

Advantageously, the tracking element 220 can be used to track motion of the oral hygiene device 210 using the method 300 (or other similar methods) without requiring any electronics or sensors (e.g., an accelerometer) in the tracking element 220. While the tracking element 220 can include such sensors in some implementations to aid in tracking motion of the oral hygiene device 210, such sensors may, for example, increase the cost of the tracking element 220, require the tracking element 220 to be charged periodically prior to use, or increase the weight of the tracking element 220 and thus interfere with a user's (e.g., a child's) brushing given the added weight at the end of the oral hygiene device 210.

While the system 100 and method 300 have been illustrated and described herein as being used to track the motion of an oral hygiene device (e.g., oral hygiene device 210), the system 100 and method 300 can be used to track the motion of any other object coupled to the tracking element 220. For example, a tracking element that is the same as or similar to the tracking element 220 can be coupled to an end of an object with a similar shape as the oral hygiene device 210, such as, for example, a baseball bat, a hockey stick, a golf club, or the like. Further, a tracking element that is similar to the tracking element 220 can more generally be attached to an object with any other shape to track the motion of the object.

While the disclosure is susceptible to various modifications and alternative forms, specific embodiments and methods thereof have been shown by way of example in the drawings and are described in detail herein. It should be understood, however, that it is not intended to limit the disclosure to the particular forms or methods disclosed, but, to the contrary, the intention is to cover all modifications, equivalents and alternatives falling within the spirit and scope of the disclosure.

Selected Embodiments

Although the above description and the attached claims disclose a number of embodiments, other alternative aspects of the present disclosure are disclosed in the following further embodiments.

Embodiment 1. A method for estimating a pose of an oral hygiene device relative to a location, the oral hygiene device including a pattern and a plurality of groups of visual markers, the method comprising: receiving image data reproducible as an image of at least a portion of the oral hygiene device; analyzing, using one or more processors, the image data to identify a region of interest within the image, the region of interest including at least a portion of the pattern therein; identifying, using at least one of the one or more processors, all candidate visual markers within the region of interest; obtaining a first proposed three-dimensional pose of the oral hygiene device; validating the first proposed three-dimensional pose of the oral hygiene device; obtaining a second proposed three-dimensional pose of the oral hygiene device based on the validated first proposed three-dimensional pose.

Embodiment 2. The method of embodiment 1, wherein responsive to identifying the region of interest, segmenting, using at least one of the one or more processors, the region of interest into a plurality of sub-regions, each of the plurality of sub-regions being defined by a plurality of pixels having a common color.

Embodiment 3. The method according to any one of embodiments 1 and 2, wherein the obtaining the first proposed three-dimensional pose of the oral hygiene device includes: creating a plurality of distinct sets of the candidate visual markers; selecting a first one of the plurality of distinct sets of the candidate visual markers; selecting a first one of a plurality of distinct sets of model markers associated with a three-dimensional model of the oral hygiene device; and evaluating a set of the candidate visual markers and a set of model markers from a three-dimensional model associated with the oral hygiene device using a perspective-three-point algorithm to obtain the proposed three-dimensional pose of the oral hygiene device.

Embodiment 4. The method according to any one of embodiments 1-3, wherein the validating the first proposed three-dimensional pose includes: based on the proposed three-dimensional pose of the oral hygiene device, predicting a position within the region of interest for a predetermined number of the candidate visual markers; and comparing the predicted positions for the predetermined number of the candidate visual markers with actual positions of all of the candidate visual markers within the region of interest; and determining that at least a substantial portion of the predicted positions correspond with the actual positions.

Embodiment 5. The method according to any one of embodiments 1-4, wherein the analyzing the first image data includes using one or more filters, the one or more filters including a movement filter, a color filter, a shape filter, or any combination thereof.

Embodiment 6. The method according to any one of embodiments 1-5, wherein the identifying all candidate visual markers is based on a shape and a color of each of the plurality of sub-regions.

Embodiment 7. The method according to any one of embodiments 1-6, wherein each of the plurality of distinct sets of the candidate visual markers includes at least four candidate visual markers and each of the plurality of distinct sets of the model markers includes at least four model markers.

Embodiment 8. The method according to any one of embodiments 1-7, further comprising: receiving a second set of image data reproducible as a second image of at least a portion of the oral hygiene device; identifying a second region of interest within the second image based on the validated three-dimensional pose of the oral hygiene device.

Embodiment 9. The method according to any one of embodiments 1-8, further comprising: adjusting, based on the validated three-dimensional pose of the oral hygiene device, a threshold for segmenting the second region of interest to aid in identifying pixels having different colors in the second region of interest.

Embodiment 10. A method for estimating a pose of an oral hygiene device relative to a location, the oral hygiene device including a pattern and a plurality of groups of visual markers, the method comprising: (a) receiving image data reproducible as an image of at least a portion of the oral hygiene device; (b) analyzing, using one or more processors, the image data to identify a region of interest within the image, the region of interest including at least a portion of the pattern therein; (c) responsive to identifying the region of interest, segmenting, using at least one of the one or more processors, the region of interest into a plurality of sub-regions, each of the plurality of sub-regions being defined by a plurality of pixels having a common color; (d) identifying, using at least one of the one or more processors, all candidate visual markers within the region of interest; (e) creating a plurality of distinct sets of the candidate visual markers; (f) selecting a first one of the plurality of distinct sets of the candidate visual markers; (g) selecting a first one of a plurality of distinct sets of model markers associated with a three-dimensional model of the oral hygiene device; (h) evaluating the selected set of the candidate visual markers and the selected set of model markers using a perspective-three-point algorithm to obtain a proposed three-dimensional pose of the oral hygiene device; (i) based on the proposed three-dimensional pose of the oral hygiene device, predicting a position within the region of interest for a predetermined number of the candidate visual markers; (j) comparing the predicted positions for the predetermined number of the candidate visual markers with actual positions of all of the candidate visual markers within the region of interest; (k) responsive to a determination that at least a substantial portion of the predicted positions correspond with the actual positions, validating the proposed three-dimensional pose; and (l) responsive to a determination that less than the substantial portion of the predicted positions correspond with the actual positions, repeating steps (f)-(k).

Embodiment 11. The method according to any one of embodiment 10, further including responsive to the proposed three-dimensional pose being validated, comparing all of the candidate visual markers and all of the model markers using an algorithm to obtain a second proposed three-dimensional pose of the oral hygiene device.

Embodiment 12. The method according to any one of embodiments 10 and 11, wherein the analyzing the first image data includes using one or more filters, the one or more filters including a movement filter, a color filter, a shape filter, or any combination thereof.

Embodiment 13. The method according to any one of embodiments 10-12, wherein the identifying all candidate visual markers is based on a shape and a color of each of the plurality of sub-regions.

Embodiment 14. The method according to any one of embodiments 10-13, wherein each of the plurality of distinct sets of the candidate visual markers includes at least four candidate visual markers and each of the plurality of distinct sets of the model markers includes at least four model markers.

Embodiment 15. The method according to any one of embodiments 10-14, further comprising: receiving a second set of image data reproducible as a second image of at least a portion of the oral hygiene device; identifying a second region of interest within the second image based on the validated three-dimensional pose of the oral hygiene device.

Embodiment 16. The method according to any one of embodiment 15, further comprising: adjusting, based on the validated three-dimensional pose of the oral hygiene device, a threshold for segmenting the second region of interest to aid in identifying pixels having different colors in the second region of interest.

Embodiment 17. A motion tracking system comprising: an oral hygiene device including a head and a handle; a tracking element coupled to the oral hygiene device including a pattern and a plurality of groups of visual markers; a camera; one or more processors; and a memory device storing instructions that, when executed by at least one of the one or more processors cause the motion tracking system to, capture, using the camera, an image of at least a portion of the oral hygiene device; analyze, using at least one of the one or more processors, the image to identify a region of interest within the image, the region of interest including at least a portion of the pattern of the tracking element therein; identify, using at least one of the one or more processors, all candidate visual markers within the region of interest; create a plurality of distinct sets of the candidate visual markers; select a first one of the plurality of distinct sets of the candidate visual markers; select a first one of a plurality of distinct sets of model markers associated with a three-dimensional model of the oral hygiene device stored in the memory device; evaluate the selected set of the candidate visual markers and the selected set of model markers using a perspective-three-point algorithm to obtain a proposed three-dimensional pose of the oral hygiene device; based on the proposed three-dimensional pose of the oral hygiene device, predict a position within the region of interest for a predetermined number of the candidate visual markers; compare the predicted positions for the predetermined number of the candidate visual markers with actual positions of all of the candidate visual markers within the region of interest; and responsive to a determination that at least a substantial portion of the predicted positions correspond with the actual positions, validate the proposed three-dimensional pose.

Embodiment 18. The system according to any one of embodiment 17, wherein the tracking element includes a cavity for receiving a portion of the handle of the oral hygiene device therein.

Embodiment 19. The system according to any one of embodiments 17 and 18, wherein the pattern of the tracking element is flush with an outer surface of the tracking element and the plurality of groups of visual markers protrude from the outer surface of the tracking element.

Embodiment 20. The system according to any one of embodiment 19, wherein the visual markers of each of the plurality of groups of visual markers have a generally dome-like shape.

Embodiment 21. The system according to any one of embodiments 17-20, wherein the pattern of the tracking element includes a background having a first color and a plurality of indicators overlaid on the background, the plurality of indicators having a second color that is different from the first color.

Embodiment 22. The system according to any one of embodiments 17-21, wherein a first group of the plurality of groups of visual markers includes a first visual marker having a first color, a second visual marker having a second color, a third visual marker having a third color, and a fourth visual marker having a fourth color.

Embodiment 23. The system according to any one of embodiments 17-22, wherein a first group of the plurality of groups of visual markers includes a first visual maker having a first color, a second visual marker having the first color, a third visual marker having the first color, and a fourth visual marker having the first color.

Embodiment 24. The system according to any one of embodiments 17-23, further comprising a mobile device including a housing, wherein the camera, the one or more processors, the memory device, or any combination thereof, are at least partially disposed within the housing of the mobile device.

Embodiment 25. A motion tracking element configured to be coupled to an oral hygiene device, the motion tracking element comprising a body, a pattern on an outer surface of the body, a plurality of groups of visual markers on the outer surface of the body.

Embodiment 26. The motion tracking element according to embodiment 25, wherein the body includes a first portion and a second portion.

Embodiment 27. The motion tracking element according to any one of embodiments 25 and 26, wherein the first portion of the body is configured to be coupled to the oral hygiene device.

Embodiment 28. The motion tracking element according to any one of embodiments 25-27, wherein the second portion of the body has a generally spherical shape.

Embodiment 29. The motion tracking element according to any one of embodiments 25-28, wherein the plurality of groups of visual markers protrude from the outer surface of the body.

Embodiment 30. The motion tracking element according to any one of embodiments 25-29, wherein the pattern is printed on the outer surface of the body.

Embodiment 31. The motion tracking element according to any one of embodiments 25-30, wherein the printed pattern includes a plurality of indicators and a background.

Embodiment 32. The motion tracking element according to any one of embodiments 25-31, wherein the background has a first color and the plurality of indicators has a second color that is different than the first color.

Embodiment 33. The motion tracking element according to any one of embodiments 25-32, wherein the plurality of groups of visual markers includes at least a first group of visual markers, a second group of visual markers, a third group of visual markers, and a fourth group of visual markers, one or more visual markers of the first group of visual markers having a first color, one or more visual markers of the second group of visual markers having a second color, one or more visual markers of the third group of visual markers having a third color, and one or more visual markers of the fourth group of visual markers having a fourth color.

Embodiment 34. The motion tracking element according to any one of embodiments 25-33, wherein the first color, the second color, the third color, and the fourth color are different and distinct from one another.

Embodiment 35. The motion tracking element according to any one of embodiments 25-34, wherein each of the first color, the second color, the third color, and the fourth color is blue, green, purple, yellow, red, orange, or any combination thereof.

What is claimed is:

1. A motion tracking element for an oral hygiene device, the motion tracking element comprising:
   a body comprising an outer surface, a portion of the outer surface comprising a pattern that includes a plurality of indicators having a non-circular shape, the indicators being flush with and forming part of the outer surface of the body; and
   a plurality of visual markers located on the portion of the outer surface of the body, each of the visual markers having a circular shape.

2. The motion tracking element according to claim 1 wherein each of the indicators has an amorphous shape.

3. The motion tracking element according to claim 1 wherein the pattern comprises a solid colored background and the plurality of indicators, the plurality of indicators having a color which contrasts with the solid colored background.

4. The motion tracking element according to claim 1 wherein the visual markers are dome-shaped members which protrude from the outer surface of the body.

5. The motion tracking element according to claim 1 wherein the body includes a first portion and a second portion, the first portion being configured to be coupled to the oral hygiene device and the second portion having a generally spherical shape, the second portion comprising the portion of outer surface of the body.

6. The motion tracking element according to claim 1 wherein the pattern is printed on the outer surface of the body and is flush with the outer surface of the body.

7. The motion tracking element according to claim 1, wherein the motion tracking element is free of any electronics or sensors.

8. A motion tracking element for detachable coupling to an oral hygiene device, the motion tracking element comprising:
   a body comprising an outer surface; and
   a plurality of visual markers located on the outer surface of the body, each of the visual markers being unitary and monolithic with the body.

9. The motion tracking element according to claim 8 wherein each of the plurality of visual markers has a circular shape, and wherein the outer surface of the body comprises a pattern that includes a plurality of indicators having a non-circular shape.

10. The motion tracking element according to claim 9 wherein the indicators are flush with and form part of the outer surface of the bod, and wherein the plurality of visual markers protrude from the outer surface of the body.

11. The motion tracking element according to claim 9 wherein each of the indicators has an amorphous shape.

12. The motion tracking element according to claim 9 wherein the pattern comprises a solid colored background and the plurality of indicators having a color which contrasts with the solid colored background.

13. The motion tracking element according to claim 8 wherein the body includes a first portion and a second portion, the first portion being configured to be coupled to the oral hygiene device and the second portion having a generally spherical shape, the plurality of visual markers being located along the second portion of the body.

14. The motion tracking element according to claim 8, wherein the motion tracking element is free of any electronics or sensors.

15. A method for estimating a pose of an oral hygiene device relative to a location, a region of the oral hygiene device comprising a plurality of visual markers, the method comprising:
   receiving image data reproducible as an image which depicts at least a portion of the region of the oral hygiene device;
   analyzing, using one or more processors, the image data to identify a region of interest within the image;
   identifying, using at least one of the one or more processors, candidate visual markers of the plurality of visual markers, the candidate visual markers being the visual markers that are located within the region of interest;

obtaining a first proposed three-dimensional pose of the oral hygiene device;

validating the first proposed three-dimensional pose of the oral hygiene device; and obtaining a second proposed three-dimensional pose of the oral hygiene device based on the validated first proposed three-dimensional pose.

16. The method according to claim 15 wherein responsive to identifying the region of interest, segmenting, using at least one of the one or more processors, the region of interest into a plurality of sub-regions, each of the plurality of sub-regions being defined by a plurality of pixels having a common color, wherein the identifying all candidate visual markers is based on a shape and a color of each of the plurality of sub-regions.

17. The method according to claim 15 wherein the obtaining the first proposed three-dimensional pose of the oral hygiene device includes:

creating a plurality of distinct sets of the candidate visual markers;

selecting a first one of the plurality of distinct sets of the candidate visual markers;

selecting a first one of a plurality of distinct sets of model markers associated with a three-dimensional model of the oral hygiene device; and evaluating a set of the candidate visual markers and a set of model markers using a perspective-three-point algorithm to obtain the proposed three-dimensional pose of the oral hygiene device.

18. The method according to claim 17 wherein each of the plurality of distinct sets of the candidate visual markers includes at least four candidate visual markers and each of the plurality of distinct sets of the model markers includes at least four model markers.

19. The method according to claim 15 further comprising:

receiving a second set of image data reproducible as a second image of at least a portion of the oral hygiene device;

identifying a second region of interest within the second image based on the validated three-dimensional pose of the oral hygiene device; and adjusting, based on the validated three-dimensional pose of the oral hygiene device, a threshold for segmenting the second region of interest to aid in identifying pixels having different colors in the second region of interest.

20. The method according to claim 15 wherein the step of obtaining the first proposed three-dimensional pose of the oral hygiene device only occurs after at least four candidate visual markers are identified.

\* \* \* \* \*